US008550990B2

(12) United States Patent
Seto et al.

(10) Patent No.: US 8,550,990 B2
(45) Date of Patent: Oct. 8, 2013

(54) ENDOSCOPE SYSTEM

(75) Inventors: Yasuhiro Seto, Kanagawa (JP); Hiroshi Murakami, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 159 days.

(21) Appl. No.: 13/182,009

(22) Filed: Jul. 13, 2011

(65) Prior Publication Data

US 2012/0016200 A1 Jan. 19, 2012

(30) Foreign Application Priority Data

Jul. 15, 2010 (JP) ................................ P2010-160681

(51) Int. Cl.
*A61B 1/06* (2006.01)

(52) U.S. Cl.
USPC .......................................... 600/180; 600/178

(58) Field of Classification Search
USPC .......... 600/103, 109, 113, 160, 178, 180–181; 362/574; 348/68–69
See application file for complete search history.

(56) References Cited

U.S. PATENT DOCUMENTS

| 7,258,663 | B2 * | 8/2007 | Doguchi et al. | 600/109 |
| 8,231,522 | B2 * | 7/2012 | Endo et al. | 600/109 |
| 2006/0017797 | A1 * | 1/2006 | Morimoto et al. | 347/237 |
| 2006/0155166 | A1 | 7/2006 | Takahashi et al. | |
| 2007/0112253 | A1 * | 5/2007 | Negishi | 600/118 |
| 2008/0021272 | A1 * | 1/2008 | Doguchi et al. | 600/109 |
| 2009/0062617 | A1 | 3/2009 | Mizuyoshi | |
| 2010/0048993 | A1 * | 2/2010 | Shidara | 600/109 |
| 2010/0240953 | A1 * | 9/2010 | Murakami | 600/109 |

FOREIGN PATENT DOCUMENTS

| JP | 2005-006974 A | 1/2005 |
| JP | 2007-111151 A | 5/2007 |
| JP | 2009-056248 A | 3/2009 |

OTHER PUBLICATIONS

U.S. Appl. No. 13/182,052, filed Jul. 13, 2011.

* cited by examiner

*Primary Examiner* — Philip R Smith
(74) *Attorney, Agent, or Firm* — McGinn IP Law Group, PLLC

(57) ABSTRACT

The endoscope system includes an endoscope, a control unit, a beam source control unit and a type check unit. The endoscope has a radiation optical system for radiating a beam from a beam source onto a subject and an imaging optical system including an imaging device. The endoscope is removably connected to the control unit. The beam source control unit controls the emission beam intensity of the beam source according to a beam quantity specified value input from the control unit. The type check unit checks a type of the imaging device mounted on the endoscope. The beam source control unit has a plurality of control patterns representing a relationship between the beam quantity specified value and a control output value, switches to any one of the control patterns according to the check results, and controls the emission beam intensity according to the switched control pattern.

8 Claims, 14 Drawing Sheets

ENDOSCOPE SYSTEM

CROSS-REFERENCE TO RELATED APPLICATIONS

This application claims the benefit of Japanese Patent Application No. 2010-160681, filed on Jul. 15, 2010, the entire contents of which are hereby incorporated by reference, the same as if set forth at length.

BACKGROUND OF THE INVENTION

1. Technical Field

The present invention relates to an endoscope system.

2. Description of Related Art

Generally, to observe tissue within a body cavity, there is used an endoscope system. The endoscope system is a system which radiates, as a radiation beam, a white beam onto a portion to be observed within the body cavity, picks up a beam image due to a reflection beam from the portion to be observed using a given imaging device which is capable of imaging a two-dimensional image, and displays the thus obtained two-dimensional image on a monitor screen. A technology for controlling the radiation beam of such endoscope system is disclosed in, for example, JP-2009-056248-A, JP-2007-111151-A and JP-2005-006974-A.

In JP-2009-056248-A, there is disclosed a technology for always obtaining a radiation beam having proper beam quantity and chromaticity. Specifically, there is proposed a technology in which a drive current to be applied to a beam source is caused to change in the form of a pulse and the pulse is controlled in the number, width and amplitude thereof.

In JP-2007-111151-A, there is disclosed a technology for supplying a radiation beam onto a diseased part while controlling the heating of an endoscope leading end. Specifically, there is proposed a technology for controlling the lighting/lighting-out of a beam source in a pulse manner and also for adjusting the lighting time of the beam source and the amplitude (intensity) of the pulse.

In JP-2005-006974-A, there is disclosed a technology which, in an endoscope apparatus corresponding to multiple observation modes, can select only the observation mode to which an endoscope connected corresponds. Here, the term "observation mode" means classification such as a normal beam observation, a fluorescence observation, a narrow bandwidth beam observation and an infrared beam observation.

Here, as an imaging device which can be used in the endoscope system in order to image the two-dimensional image, there are known a CCD (Charge Coupled Device) image sensor and a CMOS (Complementary Metal-Oxide Semiconductor) image sensor. Also, as known well, the signal reading systems of the CCD image and CMOS image sensors are different from each other because they are different in structure, and the two image sensors are also different in the shutter control in photographing.

For example, a CCD image sensor of interline transfer includes a beam receiving portion, a vertical transfer portion, a horizontal transfer portion, an amplifier and the like. Specifically, it includes the vertical transfer portion which is capable of holding electric charges with respect to all pixels within the beam receiving portion. Therefore, after completion of exposure, electric charges accumulated in the respective pixels can be transferred to the vertical transfer portion respectively at the same timing. Accordingly, the timing for starting the accumulation of electric charges in the respective pixel positions of the beam receiving portion is the same in all pixels. And, the timing for ending the accumulation of the electric charges is the same in all pixels. That is, when imaging the two-dimensional image, by controlling only the image sensor, the shutter can be released at the same time for the whole of 1 frame of the two-dimensional image. This shutter control system is called a global shutter system.

On the other hand, in the case of an ordinary CMOS image sensor, from the respective pixel positions of a beam receiving unit having a two-dimensional arrangement constituted of N lines and M rows, there are read out electric charges sequentially line by line, and electric charges simultaneously accumulated are initialized. Therefore, the timing for starting the accumulation of electric charges at the respective pixel positions of the beam receiving portion is caused to shift slightly from each other every line. And, the timing for ending the charge accumulation is caused to shift slightly from each other every line. That is, when imaging the two-dimensional image, only through control of the image sensor side, the timings for releasing the shutter are caused to shift every line in the two-dimensional image, whereby the shutter cannot be released simultaneously for the whole of 1 frame. This shutter control system is called a rolling shutter system.

Therefore, in the case of an endoscope system employing an ordinary CMOS image sensor, the timings in the charge accumulation period (the time during which the shutter is substantially opened) at the respective positions of the beam receiving portion is different every scan line. Therefore, in the case that the on start timing of the beam source is adjusted in order to control the radiation beam, the radiation beam quantity varies every scan line of the two-dimensional image, thereby causing the luminance of the image to vary.

In the case that only the amplitude (beam emission intensity) of a current to be supplied to the beam source is controlled, since the radiation beam quantity is not influenced by the difference of the timings for signal reading or the like, even in an endoscope system employing an ordinary CMOS image sensor, there is no possibility that the luminance can vary every scan line. However, in the endoscope system, generally, there is required a beam quantity dynamic range of 1:9000 or more. Such broad beam quantity dynamic range cannot be realized only by controlling the amplitude of a current to be supplied to the beam source.

On the other hand, in an endoscope system employing a CCD image sensor, since the timings for signal reading and the like is not different every scan line, the on start timings of the beam source can also be adjusted in order to control a beam for radiation. Also, in an endoscope system employing a CCD image sensor, since there exists the time during which the shutter is closed simultaneously for all pixels, during this time, unnecessary radiation can be turned off, which is useful in controlling heat generation. However, in an endoscope system employing an ordinary CMOS image sensor, since the time during which the shutter is closed varies every scan line, radiation cannot be turned off during a specific period.

SUMMARY

As described above, depending on the type of an imaging device mounted on an endoscope used, the optimum control of a radiation beam is changed. However, the optimum control of the emission beam quantity of a radiation beam according to the type of an imaging device has not been performed.

Thus, it is an object of the invention to provide an endoscope system which is capable of controlling the beam quantity of a radiation beam properly in a broad dynamic range according to the type of an imaging device mounted on an endoscope.

The present invention is constituted of the following features.

An endoscope system includes an endoscope, a control unit, a beam source control unit and a type check unit. The endoscope includes a radiation optical system for radiating a beam emitted from a beam source onto a subject and an imaging optical system containing an imaging device for imaging the subject. The endoscope removably connects to the control unit. The beam source control unit controls emission beam intensity of the beam source according to a beam quantity specified value input from the control unit. The type check unit checks a type of the imaging device mounted on the endoscope which is connected to the control unit. The beam source control unit has a plurality of control patterns for expressing a relationship between the beam quantity specified value and a control output value to be given to the beam source, switches to any one of the control patterns according to the check result obtained by the type check unit, and controls the emission beam intensity of the beam source according to the switched control pattern.

According to the endoscope system of the invention, since the control pattern of a radiation beam is switched according to the type of an imaging device mounted on an endoscope which is connected to the system, the control of the radiation beam can be performed properly according to the type of an imaging device, and the beam quantity control in a broad dynamic range can be realized.

DETAILED DESCRIPTION OF EMBODIMENTS OF THE INVENTION

Now, description will be given below specifically of an embodiment according to the invention with reference to the accompanying drawings.

Figure 1:
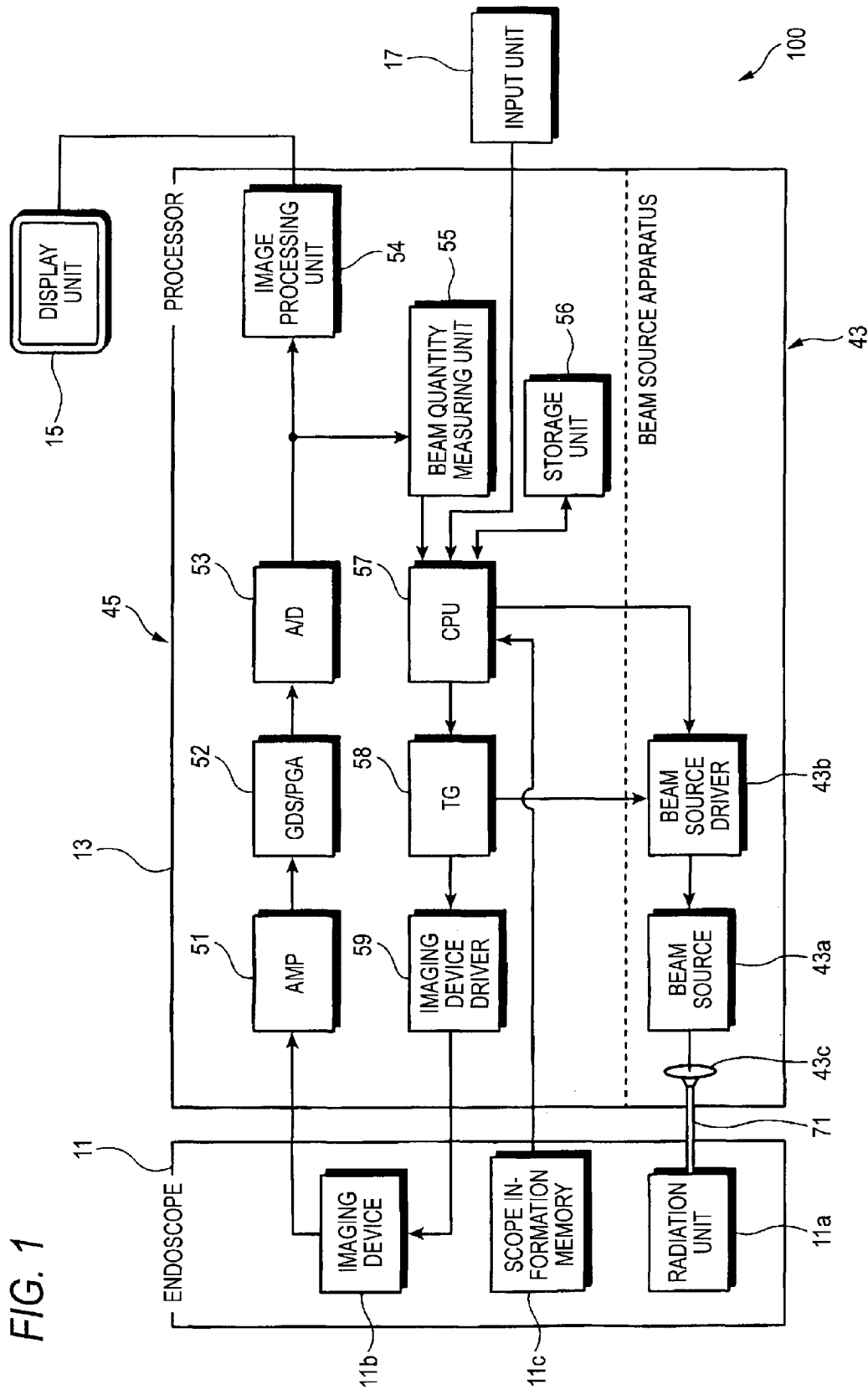
FIG. 1 is a block diagram of an example of the structure of the main portions of the whole of an endoscope system according to an embodiment of the invention.

An example of the structure of the main portions of the whole endoscope system according to the present embodiment is shown in FIG. 1. Also, the appearance of the endoscope system shown in FIG. 1 is shown in FIG. 2.

Figure 2:
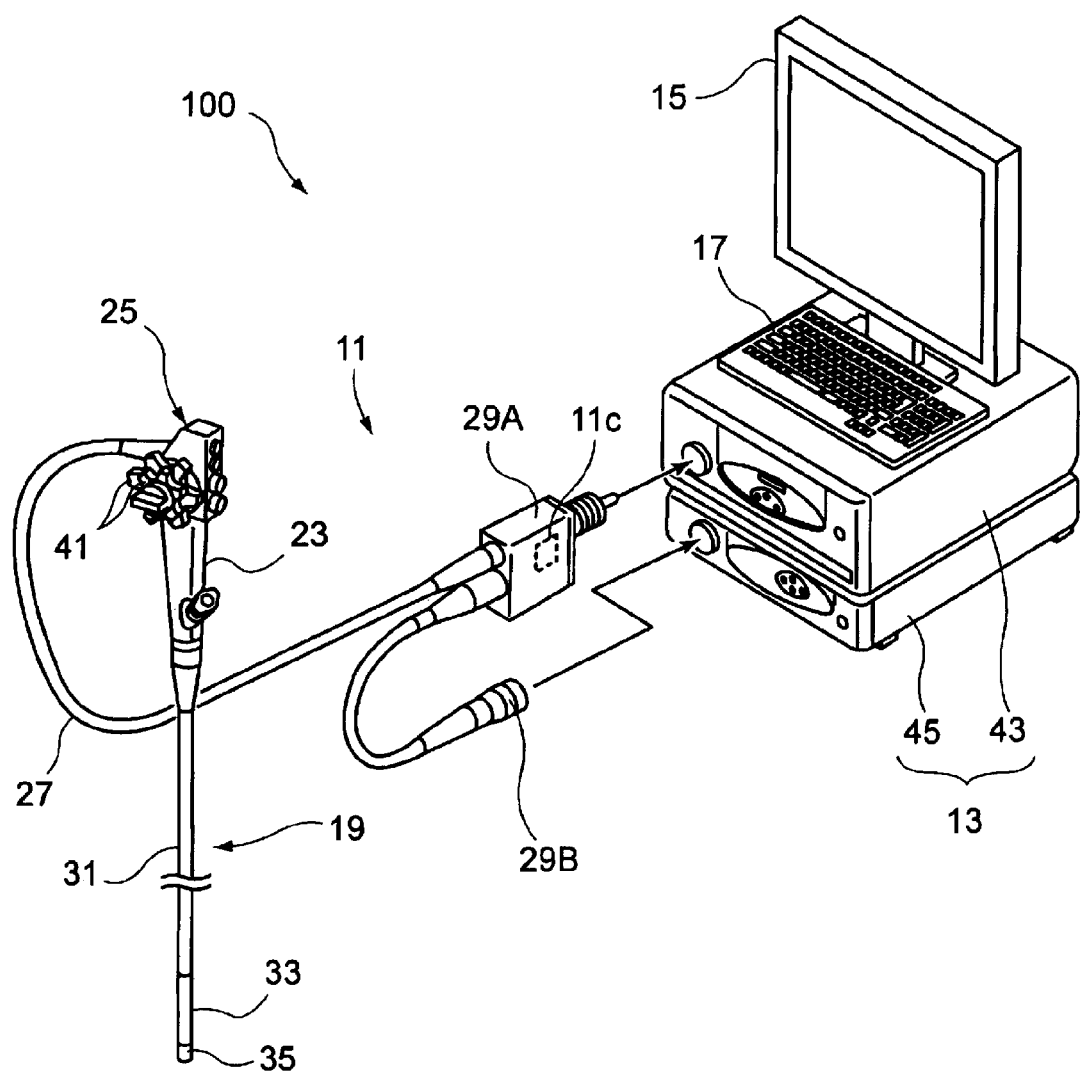
FIG. 2 is a perspective view of the appearance of the endoscope system shown in FIG. 1.

As shown in FIGS. 1 and 2, an endoscope system 100 includes an endoscope 11, a control unit 13 as an external control unit to which the endoscope 11 can be connected, and a display unit 15 connected to the control unit 13 for displaying image information. And, an input unit 17 is connected to the control unit 13 for accepting an input operation.

The endoscope 11 is an electronic endoscope which, as shown in FIG. 1, includes a radiation unit 11a (a radiation optical system), an imaging device 11b (an imaging optical system) and a scope information memory 11c. The radiation unit 11a emits a radiation beam from the leading end of an endoscope insertion unit 19 shown in FIG. 2. The imaging device 11b is a two-dimensional imaging device which can pick up the image of an area to be observed of a living body or the like through a given object lens unit to thereby obtain a two-dimensional image. As a specific example of the imaging device 11b, there can be used a two-dimensional CCD (Charge Coupled Device) image sensor or a two-dimensional CMOS (Complementary Metal-Oxide Semiconductor) image sensor.

Here, in the endoscope system 100, normally, it is necessary to reproduce a color image. Thus, as the imaging device 11b, actually, there is used an imaging device of a single plate color imaging optical system including a color filter (for example, a Bayer-arranged RGB original color filter, or a CMYG, CMY complementary color filter) constituted of multiple color segments.

The scope information memory 11c previously stores information inherent to the endoscope 11. In the information which the scope information memory 11c stores, there is also included information about the shutter system of the imaging device 11b.

The endoscope 11, as shown in FIG. 2, includes an endoscope insertion unit 19, an operation unit 25, a universal code 27, and connector units 29A & 29B. The endoscope insertion unit 19 is formed to have a long and narrow shape and the leading end side thereof can be inserted into a subject. Also, the endoscope insertion unit 19 is constituted of a flexible soft portion 31, a curved portion 33 and a leading end portion (which is also hereinafter referred to as an endoscope leading end portion). The operation unit 25 is connected to the base end portion of the endoscope insertion unit 19 and is used to perform the curving operation of the leading end of the endoscope insertion unit 19 and an operation for observation. The universal code 27 is extended from the operation unit 25. The connector units 29A and 29B are respectively provided on the leading end of the universal code 27 and are used to connect the endoscope 11 to the control unit 13 removably.

The curved portion 33 is interposed between the soft portion 31 and endoscope leading end portion 35 and can be curved by rotating an angle knob 41 provided on the operation unit 25. The curved portion 33 can be curved in an arbitrary direction and at arbitrary angle according to the portion of the subject to which the endoscope 11 is applied, thereby being able to set the radiation direction of the radiation window for radiation of the endoscope leading end portion 35 and the observation direction of the imaging device to a desired observation portion.

Figure 3:
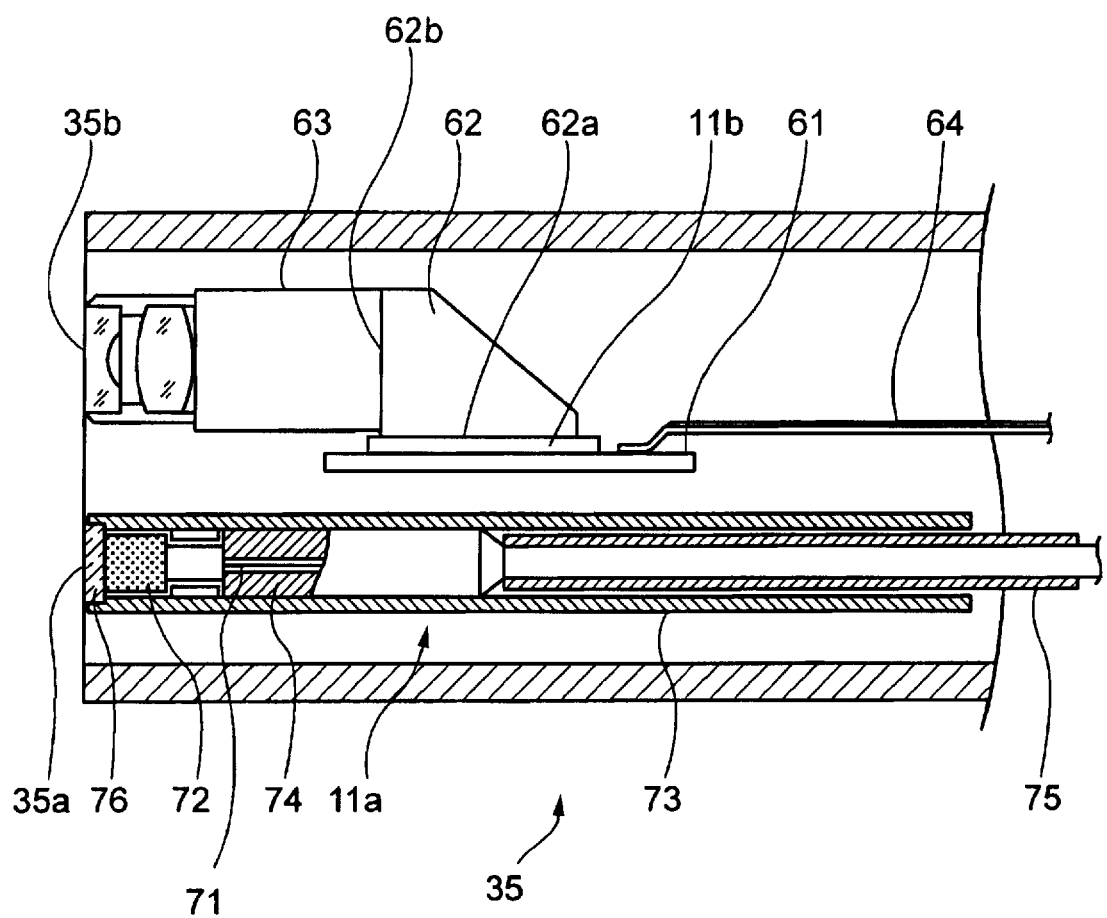
FIG. 3 is a longitudinal section view of the neighboring structure of the leading end portion of an endoscope.

FIG. 3 shows the structure of the neighboring portion of the endoscope leading end portion 35. As shown in FIG. 3, in the endoscope leading end portion 35, there are formed a radiation unit 11a for radiating a radiation beam onto the area to be observed and an imaging device 11b for picking up the image of the area to be observed.

The radiation unit 11a includes a multi-mode optical fiber 71 and a fluorescent member 72. As the multi-mode optical fiber 71, for example, there can be used a small diameter optical fiber which has a core diameter of 10 μm, a clad diameter of 125 μm, and a diameter of 0.3 mm~0.5 mm when including a protection layer serving as a coating.

The multi-mode optical fiber 71 guides a blue beam, which is emitted from a beam source 43a disposed within a beam source apparatus 43, to the vicinity of the fluorescent member 72 of the endoscope leading end portion 35. The fluorescent member 72 absorbs part of the energy of the blue beam guided by the multi-mode optical fiber 71 and is thereby excited to generate a visible beam having a wavelength band ranging from green~yellow. The fluorescent member 72 is made of plural fluorescent materials; and, for example, it may include a YAG system fluorescent member or a fluorescent material such as AM ($BaMgAl_{10}O_{17}$).

As shown in FIG. 3, there is provided a cylindrical sleeve member 73 in such a manner that it covers the outer periphery of the fluorescent member 72. Into the sleeve member 73, there is inserted a ferrule 74 which is used to hold the multi-mode optical fiber 71 in such a manner that it serves as the center shaft of the multi-mode optical fiber 71. Further, into such portion of the multi-mode optical fiber 71 as is extended from the rear end side (which is opposite to the leading end side) of the ferrule 74, there is provided a flexible sleeve 75 for covering the coating of the multi-mode optical fiber 71 in such a manner that it is interposed between the sleeve member 73 and the multi-mode optical fiber 71.

An emission beam which is generated in the fluorescent member 72 due to excitation and part of the blue beam which is guided by the multi-mode optical fiber 71 and which is transmitted through the fluorescent member 72 are combined together, and the thus combined beam is emitted from the radiation window 35a toward the area to be observed as a radiation beam having a spectrum near white. In the vicinity of the radiation window 35a, a radiation lens 76 is provided for radiating the radiation beam.

As shown in FIG. 3, the imaging device 11b is disposed on a base plate 61 which is fixed to the inside of the endoscope leading end portion 35. Also, to the beam receiving surface of the imaging device 11b, there is connected one end face 62a of a prism 62. And, to the other end face 62b extending at right angles to the end face 62a, there is connected an object lens unit 63. In order to be able to pick up the image of the area to be observed from an observation window 35b which is formed to face the area to be observed, the object lens unit 63 guides its beam to the beam receiving surface of the imaging device 11b through the prism 62. A signal cable 64 is used to connect the imaging device 11b on the base plate 61 to the control unit 13 electrically.

Referring back again to FIG. 1, the control unit 13 is constituted of a video processor 45 and a beam source apparatus 43. The beam source apparatus 43 is used to emit a radiation beam to be supplied to the radiation window of the endoscope leading end portion 35. The video processor 45 functions a beam controller which image processes an image signal to be output from the imaging device 11b and also controls the beam quantity for radiation. The video processor 45 and beam source apparatus 43, as shown in FIG. 2, are respectively connected to the endoscope 11 through the connector units 29A and 29B.

Also, to the video processor 45, there are connected the above-mentioned display unit 15 and input unit 17. The video processor 45, according to an instruction from the operation unit 25 or input unit 17 of the endoscope 11, image processes an image pickup signal transmitted from the endoscope 11, generates a display image and supplies it to the display unit 15.

Next, description will be given below of the signal processing of the endoscope system.

As shown in FIG. 1, the video processor 45 includes an amplifier (AMP) 51, a correlated double sampling/programmable gain amplifier (which is hereinafter referred to as CDS/PGA) 52, an A/D converter 53, an image processing unit 54, a beam quantity measuring unit 55, a storage unit 56, a microcomputer (CPU) 57, a timing generator (TG) 58, and an imaging device driver 59.

To the input of the amplifier 51, there is input an image pickup signal which can be obtained through the photographing of the imaging device 11. After the image pickup signal is amplified by the amplifier 51 having a constant gain, it is input to CDS/PGA 52. CDS/PGA 52 inputs therein an image pickup signal amplified by the amplifier 51 and outputs it as an analog image signal representing the levels of the respective colors, that is, R (red), G (green) and B (blue) respectively corresponding accurately to the accumulated electric charges of the respective photoelectric conversion cells of the imaging device 11b.

The analog image signal output from CDS/PGA 52 is input to the A/D converter 53, where it is converted to digital image data. The image processing unit 54 performs various image processings on the digital image data output from the A/D converter 53 to generate information about the image to be displayed on the screen of the display unit 15. Therefore, on the display unit 15, there is displayed an image picked up by the imaging device 11b of the endoscope 11, that is, the two-dimensional image of the area to be observed of a living body.

To a control input terminal used to control the photographing of the imaging device 11b and signal read-out, there is connected the output of the imaging device driver 59. Also, to the input of the imaging device driver 59, there is connected the output of the timing generator 58. The imaging device driver 59, using various timing signals (clock pulses) input from the timing generator 58, controls various kinds of timing in the photographing of the imaging device 11b. That is, it controls timing for reading out signal charges accumulated in the respective cell areas through the photographing and the shutter speed of an electronic shutter. The timing generator 58 also generates a timing signal which is given to the beam source driver 43b.

In the video processor 45 according to the present structure example, the timing generator 58 is structured in the following manner. That is, even in the case that the endoscope 11 mounts thereon any one of the CCD image sensor and CMOS image sensor as the imaging device 11b, the timing generator 58 can output a timing signal necessary to perform a desired photographing operation. Switching between the control for the CCD image sensor and the control for the CMOS image sensor over to each other can be performed according to an instruction which is input to the timing generator 58 from the microcomputer 57.

In a CCD image sensor of a global shutter system, exposure operations with respect to the respective cells of the all pixels are performed at the same timing, whereas, in a CMOS image sensor of an ordinary rolling shutter system, exposure operations and signal read-out operations must be performed sequentially while varying the timings every scan line (every line). Therefore, the timing generator 58 is structured such that it can be selectively applied to the two systems. Here, the CMOS image sensor includes an image sensor of a global shutter system and, in this case, the CMOS image sensor of a global shutter system should be treated similarly to the CCD image sensor of a global shutter system.

The beam quantity measuring unit 55 measures a beam quantity according to the digital image data output from the A/D converter 53. For example, it detects the maximum luminance, minimum luminance, average luminance and the like of the whole area from the digital image data output obtained by photographing to thereby be able to determine whether an image having desired brightness has been picked up or not.

In the storage unit 56, there are stored various control patterns representing the relationship between a beam quantity specified value to be instructed to the beam source driver 43b for beam control and a control output value to be output to the beam source 43a. Based on the type of the endoscope, namely, in linking with the shutter operation of the imaging device 11b of the endoscope 11, that is, according to whether the imaging device has a CCD image sensor of a global shutter system or a CMOS image sensor of a rolling shutter system, a control pattern corresponding to the type of the current imaging device is taken out and is transmitted to the beam source driver 43b. Here, this control pattern may also is stored in the beam source driver 43b.

The microcomputer 57 executes a previously predetermined program to thereby control the whole of the endoscope system 100. Typical processings to be executed under the control of the microcomputer 57 are as follows.

1. The microcomputer 57 reads the information of the endoscope 11 connected to the control unit 13 from the scope information memory 11c of the endoscope 11. In this information, there are contained the contents indicating whether the electronic shutter control system is a global shutter system or a rolling shutter system.

2. The microcomputer 57, according to the above read information, provides an instruction to the timing generator 58. The instruction indicates that the imaging device driver 59 is allowed to drive the imaging device 11b according to a global shutter system or a rolling shutter system.

3. According to an instruction on a shutter speed and the like input from the input unit 17 based on the operation of a user, the microcomputer 57 provides another instruction to the timing generator 58. The instruction indicates that the imaging device driver 59 should drive the imaging device 11b at the instructed shutter speed.

4. According to the above read information, the microcomputer 57 automatically selects one of the plural control patterns which are stored in the storage unit 56. Due to this, there are selected control patterns which are different between a global shutter system and a rolling shutter system.

5. The microcomputer 57 provides an instruction to the beam source apparatus 43 such that the beam source apparatus 43 should control the beam quantity according to a beam quantity specified value for radiation control, which is determined by a beam quantity measured by the beam quantity measuring unit 55 or by a specified value input from the input unit 17, and according to a predetermined control pattern.

As shown in FIG. 1, the beam source apparatus 43 includes a beam source 43a, a beam source driver 43b and a condenser lens 43c. In the case that the beam source 43a is electrically energized under the control of the beam source driver 43b, the beam source 43a generates a beam and emits this beam therefrom. This beam is condensed by the condenser lens 43c and is then guided into an optical fiber 71. And, the beam is transmitted through the optical fiber 71 and is then guided to the radiation unit 11a.

Here, according to the present embodiment, as the beam source 43a, there is used a blue LED (light emitting diode) having an oscillation wavelength of 405 nm or 445, or an LD (laser diode), for example, an InGaN system laser diode of a broad area type, an InGaNAs system laser diode, or a GaNAs system laser diode.

The beam source driver 43b is connected to the timing generator 58 and microcomputer 57 of the video processor 45. According to an instruction given from the microcomputer 57 and the timing of the signal input from the timing generator 58, the beam source driver 43b supplies a pulse-shaped drive current to the beam source 43a. The contents of the control of the beam source driver 43b, as will be discussed later, are automatically switched between the global shutter system and rolling shutter system.

Figure 4:
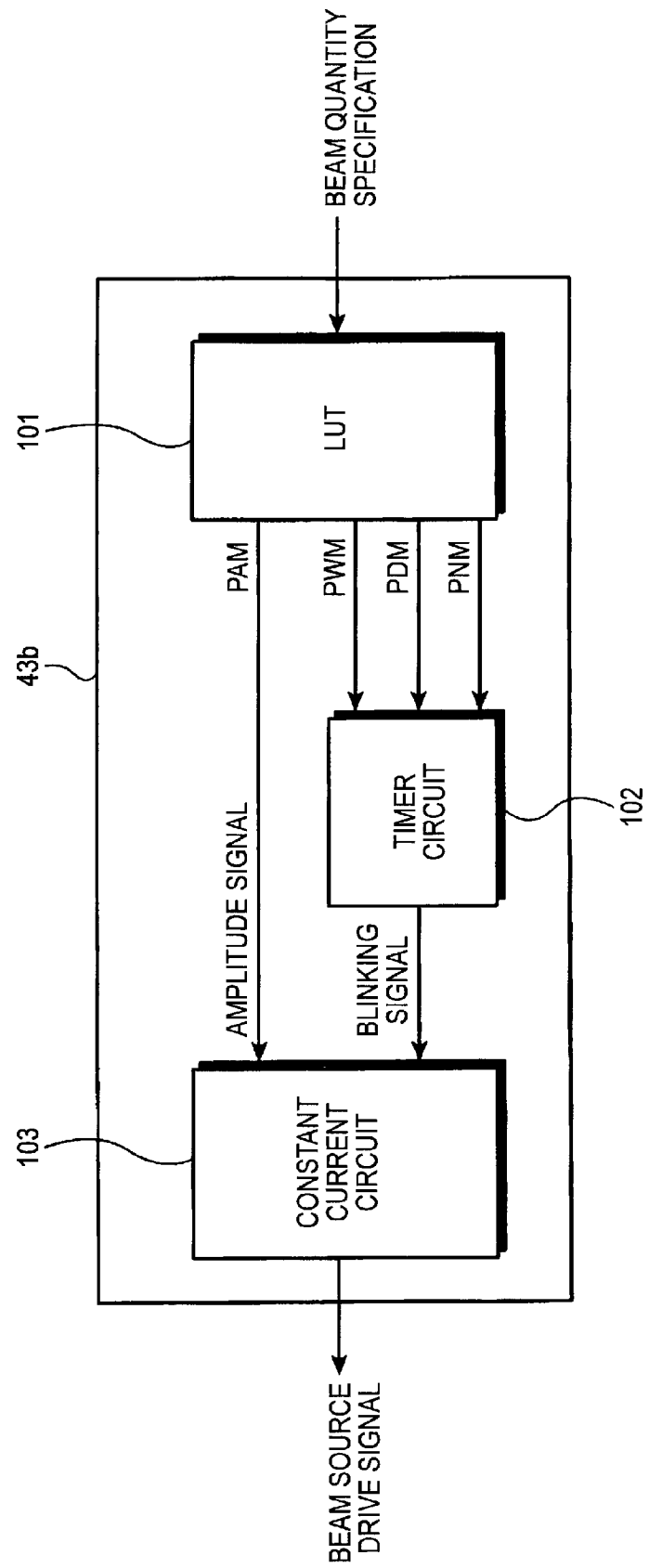
FIG. 4 is a block diagram of a specific structure example of a beam source driver.

FIG. 4 shows an example of the specific structure of the beam source driver 43b. In the example shown in FIG. 4, the beam source driver 43b includes an LUT (lookup table) 101, a timer circuit 102 and a constant current circuit 103.

The beam source driver 43b can combine pulse number modulation (PNM) control, pulse width modulation (PWM) control, pulse amplitude modulation (PAM) control and pulse density modulation (PDM) control as occasion demands, thereby being able to generate a beam source drive signal for controlling the current of the beam source 43a. The contents of the respective pieces of PAM, PWM, PDM and PNM control will be described later.

In LUT 101, there are registered multiple combinations of PAM, PWM, PDM and PNM control as control patterns. The plural control patterns respectively specify the emission beam intensity of a beam source as any one or the combination of two or more of control amount corresponding to pulse number modulation (PNM) control, control amount corresponding to pulse width modulation (PWM) control, control amount corresponding to pulse amplitude modulation (PAM) control and control amount corresponding to pulse density modulation (PDM) control with respect to a beam quantity specified value. By controlling the beam source through combinations of the plural controls, the dynamic range of the emission beam quantity of the beam source can be enlarged.

Here, LUT 101 may also be structured such that it not only stores the respective control amounts as a table but also it obtains the respective control amounts according to an operation equation.

According to the control values of PAM, PWM, PDM and PNM respectively input from LUT 101 and the timing of a signal input from the timing generator 58, the timer circuit 102 provides a blinking signal to the constant current circuit 103 for supplying a pulse-shaped drive current to the beam source 43a.

According to an amplitude signal corresponding to the control value of PAM input from LUT 101 and a blinking signal output from the timer circuit 102, the constant current circuit 103 generates a beam source drive signal for controlling the current of the beam source 43a.

Figure 5:
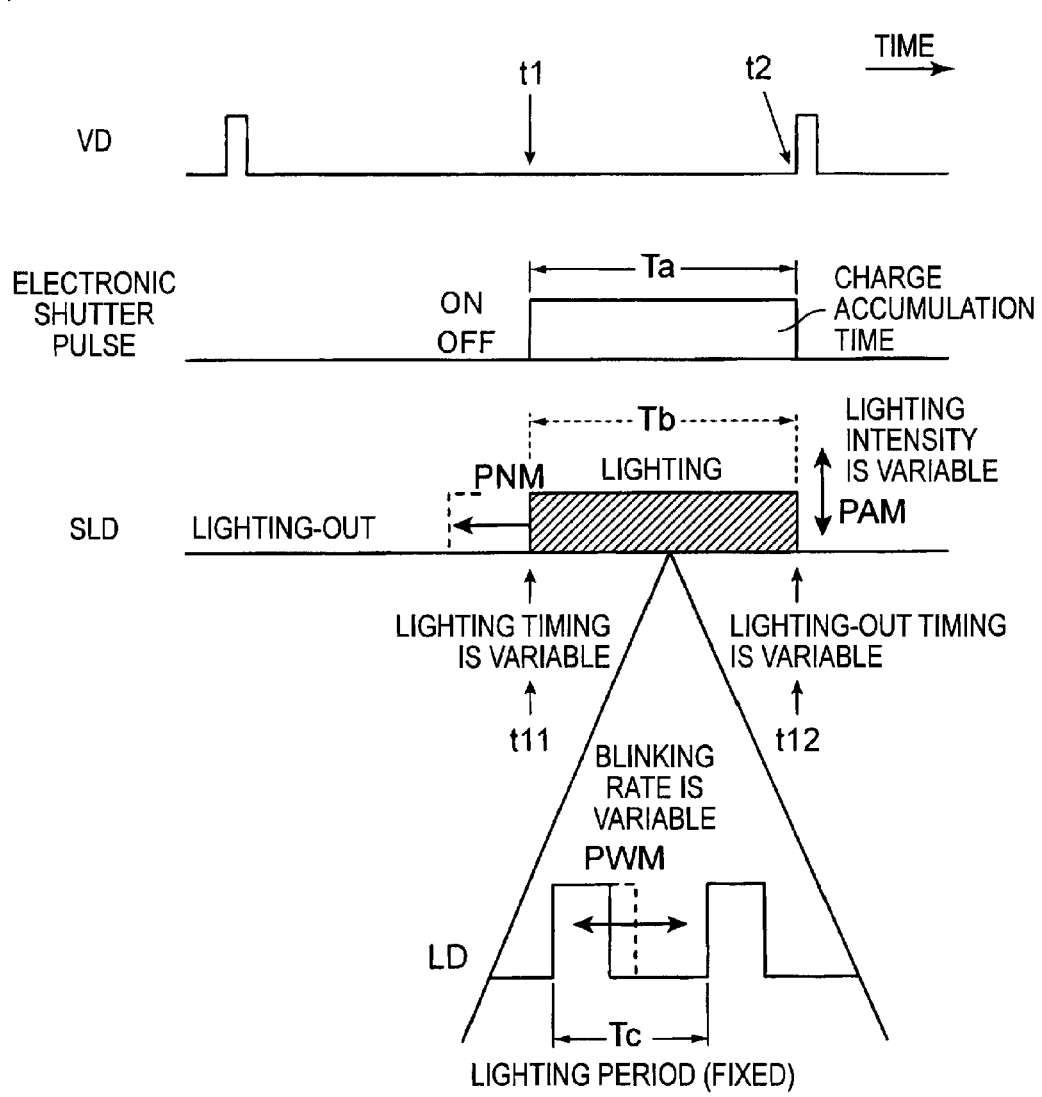
FIG. 5 is a time chart of an example of control timing when controlling the quantity of a radiation beam according to a global shutter system.

FIG. 5 shows an example of control timing in a case where the electric charge accumulation period of the photoelectric conversion portion of the imaging device is controlled by an electronic shutter of a global shutter system, as in a case where the imaging device 11b of the endoscope 11 connected to the control unit 13 is an image sensor of a CCD type.

In FIG. 5, there are shown a vertical scan signal VD for controlling the scan of the imaging device 11b, an electronic shutter pulse, and the drive signal SLD (corresponding to the beam source drive signal shown in FIG. 4) of the laser diode LD serving as the beam source for radiation (corresponding to 43a shown in FIG. 1). Also, in the vertical scan signal VD shown in FIG. 5, the duration between one pulse and next pulse represents the time of 1 screen (1 frame).

And, during the lighting time (Ta) of the electronic shutter pulse, in such area of a cell as corresponds to each pixel of the photoelectric conversion portion of the imaging device 11b, electric charges are generated and accumulated, which corresponds to the received beam intensity and exposure time (corresponding to Ta) by a photo diode or the like. In this case, since the electronic shutter employs a global shutter system, the electric charges of all pixels are accumulated at the same timing. That is, in each of a large number of pixels, the charge accumulation starts at the time t1 shown in FIG. 5 and ends at the time t2 when the time passes the time Ta of the electronic shutter.

Since radiation in this case has no influence on the image to be picked up except for the time when the electronic shutter is opened, the beam source drive signal SLD for controlling the radiation beam is controlled to turn on the beam source in such a manner that its turn-on-timing is so adjusted as to synchronize with the timing (t1~t2) of the charge accumulation of the imaging device 11b.

In the example shown in FIG. 5, there is assumed a case where the beam quantity of radiation is controlled by combining the pulse number modulation (PNM) control, pulse width modulation (PWM) control and pulse amplitude modulation (PAM) control.

That is, the time t11 for switching the beam source drive signal SLD shown in FIG. 5 from lighting-out (low level) to lighting (high level) is changed to around the time t1 for opening the electronic shutter, whereby the length of the lighting time Tb can be adjusted, thereby being able to control the beam amount. The time t12 for switching the beam source drive signal from lighting to lighting-out is fixed to the same timing as the time t2. The lighting time Tb is controlled to integer multiples of the lighting-cycle Tc of the PWM control. This is PNM control. Here, the lighting time Tb is set at a ratio which is larger than a predetermined ratio with respect to the charge accumulation time Ta per frame. For example, in the case that the predetermined ratio is set for ½, a discontinuous feeling in the moving image reproduction can be prevented and the occurrence of blinking can also be prevented.

Also, even during the lighting time Tb from time t11 to t12 shown in FIG. 5, at every a certain lighting-cycle Tc (for example, about ¹⁄₁₀₀ of Tb) which is very short, the on/off of the beam source drive signal SLD is controlled to repeat lighting and lighting-out alternately. And, during the respective periods of the lighting-cycle Tc, the width of a pulse representing the time for actually turning on the signal SLD is adjusted. The beam quantity (blinking ratio) is controlled in this manner. This is PWM control.

Also, since the amplitude of the pulse (during t11 and t12) of the beam source drive signal SLD is variable, the intensity (instantaneous value) of the current to be applied to the beam source can be changed, thereby being able to adjust the lighting intensity of the beam source. This is PAM control.

Figure 6:
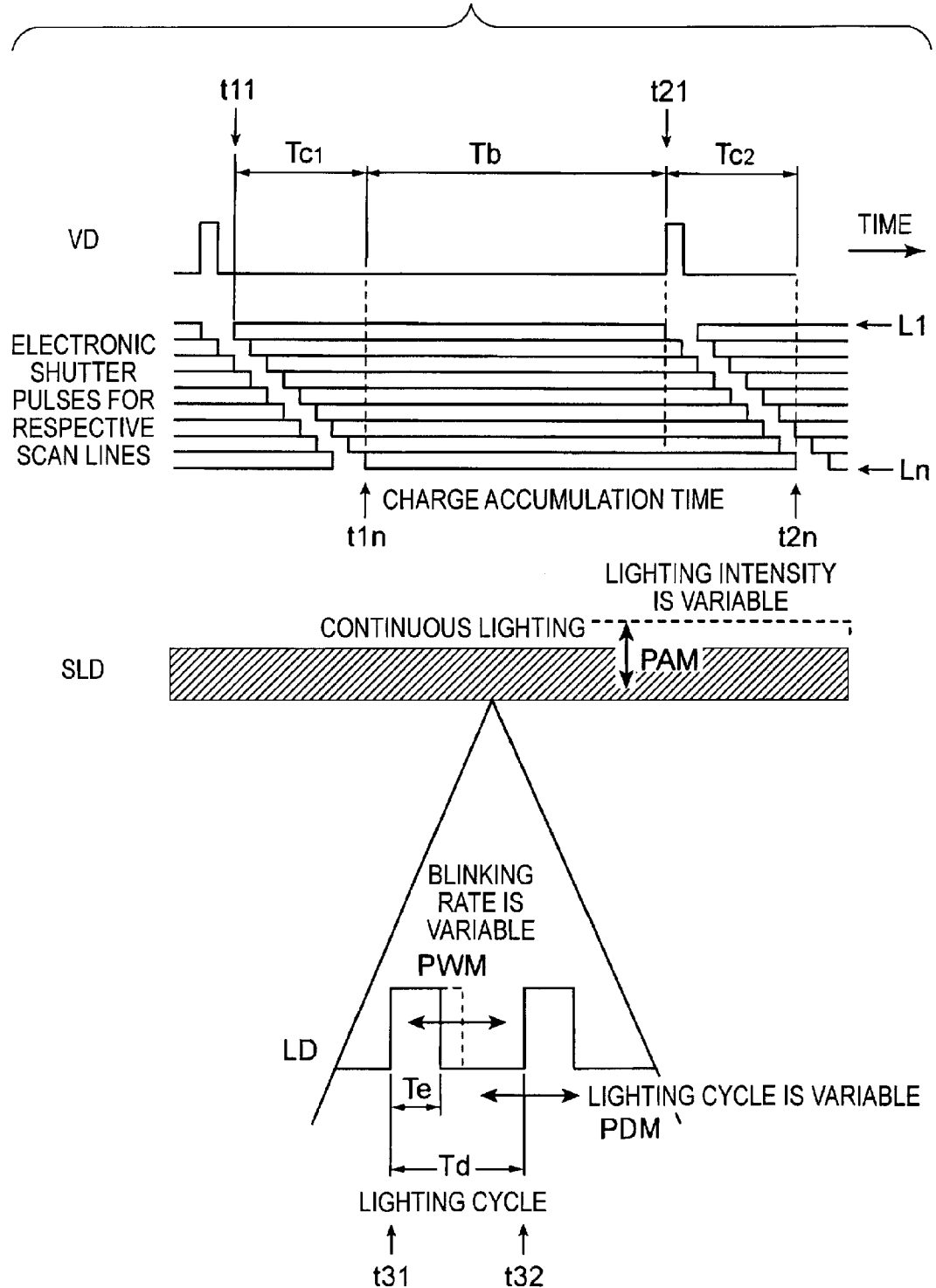
FIG. 6 is a time chart of an example of control timing when controlling the quantity of a radiation beam according to a rolling shutter system.

FIG. 6 shows an example of control timing in which the imaging device 11b of the endoscope 11 connected to the control unit 13 is an image sensor of a CMOS type and the charge accumulation time of the photoelectric conversion portion of the imaging device is controlled by an electric shutter of a rolling shutter system.

In FIG. 6, there are shown a vertical scan signal VD for controlling the scan of the imaging device 11b, electronic shutter pulses to be applied to each of a large number of scan lines, and the drive signal SLD (corresponding to the beam source drive signal shown in FIG. 4) of a laser diode LD serving as a beam source for radiation (43a in FIG. 1). The time between one pulse and its next pulse in the vertical scan signal VD shown in FIG. 6 represents the period of 1 screen (1 frame).

In the case of an ordinary image sensor of a CMOS type, since there is no element which can hold simultaneously signal charges generated at the respective pixel positions of the photoelectric conversion portion of the imaging device for all pixels, it is necessary to perform the charge accumulation and signal charge read-out sequentially on every line of a large number of pixel groups arranged in the line and row directions. Therefore, in this case, the scan is controlled by an electronic shutter of a rolling shutter system.

In this case, as shown in FIG. 6, the timing of the electronic shutter pulses to be applied to the imaging device 11b is shifted slightly in every scan line (every line of the pixel groups). For example, in the first scan line L1, the electronic shutter pulse opens the shutter at the time t11 and closes the shutter at the time t21, whereas, in the n-th scan line Ln, the electronic shutter pulse opens the shutter at the time t1n and closes the shutter at the time t2n. That is, the shutter-opening time t1n and shutter-closing time t2n of the n-th scan line Ln are delayed in timing by the time Tc1 and time Tc2 respectively with respect to the first scan line L1. The period from the time when the electronic shutter is opened to the time when it is closed (for example, in FIG. 6, "Tc1+Tb1"), that is, the lengths of the charge accumulation periods of the respective pixel positions are the same in all scan lines.

For example, as shown in FIG. 6, in the case that the charge accumulation periods of the respective pixel positions are equal to the period of 1 frame (an interval between the pulses of the vertical scan signal VD), at any timing, when the beam source of radiation is turned off, its influence appears as a variation in the charge accumulation periods of the respective pixel positions of the imaging device 11b. Also, since the charge accumulation periods are shifted in the timing in every line, according to the timing at which the beam source of radiation is turned off, different influences appear in each of the lines of the imaging device 11b.

Therefore, in the example shown in FIG. 6, the drive signal SLD of the laser diode LD for radiation is controlled in such a manner that the beam source can be turned on substantially continuously. Thus, in the example shown in FIG. 6, although the above-mentioned pulse number modulation (PNM) control is not performed, the pulse width modulation (PWM) control, pulse amplitude modulation (PAM) control and pulse density modulation (PDM) control are performed.

That is, even during the period (whole period) during which the beam source is on, lighting and lighting-out are cyclically repeated at a very short cycle, thereby controlling the drive signal SLD to blink the beam source. In other words, during the lighting cycle Td from the time t31 to the time t32 shown in FIG. 6, the on and off of the beam source drive signal SLD are controlled to lighting and lighting-out, thereby adjusting the width of a pulse expressing the time for actually lighting the beam source. The beam quantity (blinking ratio) is controlled in this manner. This is PWM control.

Also, the lighting cycle Td that is used in PWM control is not constant but is variable. The control that adjusts the lighting cycle Td is PDM control. That is, even in the case that the pulse width (lighting period Te) in the lighting cycle Td is constant, when the lighting cycle Td elongates, the beam quantity for radiation decreases; and, when the lighting cycle Td is shorten, the beam quantity for radiation increases. Also, in the case that the width of the pulse of the beam source drive signal SLD is set variable, the intensity (instantaneous value)

of a current to be applied to the beam source can be changed, thereby being able to adjust the on intensity of the beam source. This is PAM control.

Here, in the example shown in FIG. 6, while the beam source drive signal SLD is controlled such that the beam source for radiation should be turned on continuously, alternatively for example, the beam source for radiation may be on only during the time of a period Tb shown in FIG. 6 and may be off during other periods. That is, avoiding the timing (during the respective periods Tc1 and Tc2) for switching the lines in the rolling shutter control of the imaging device $11b$, the beam source may be turned on at other remaining timing. In this case, even in the rolling shutter control, the lengths of the actual exposure times (charge accumulation periods) of the respective lines can be made to coincide and the execution of the above-mentioned pulse number modulation (PNM) control is also possible. That is, without being conscious of the timing for switching the lines in the rolling shutter control, the beam quantity for radiation can be controlled.

As described above, the microcomputer 57 shown in FIG. 1 functions as a type check unit and reads information about the endoscope 11 from the scope information memory $11c$ of the endoscope 11 connected to the control unit 13 so as to check whether the electronic shutter control system of the imaging device $11b$ of the endoscope 11 is a global shutter system or a rolling shutter system. And, the microcomputer 57 automatically switches a beam control cable for controlling the beam source $43a$ for radiation in linking with the electronic shutter operation of the imaging device, that is, according to its check of the imaging device $11b$ for the global shutter system or rolling shutter system.

The beam control table represents the relationship between a beam quantity specified value for controlling the beam quantity of the beam source $43a$ and a control output value, while the table is provided on, for example, LUT 101 shown in FIG. 4. The control output value of the beam control table is constituted of any one of a control value for PAM control, a control value for PNM control, a control value for PWM control, and a control value for PDM control, or plural combinations thereof. In order that the relationship between the beam quantity specified value and control output value can be switched selectively among plural control patterns, there are previously prepared multiple beam control tables. According to cases, that is, according to imaging conditions including the distinction between the global shutter system and rolling shutter system of the imaging device $11b$ of the endoscope and other photographing conditions, the microcomputer 57 automatically selects one of the multiple beam control tables and makes it usable.

Figure 7:
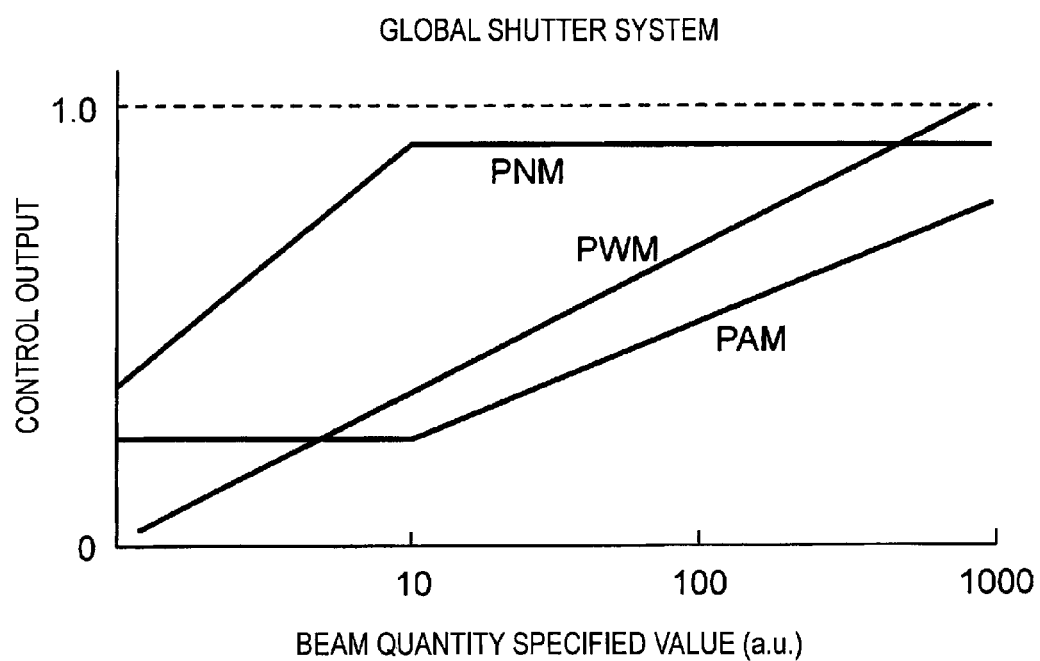
FIG. 7 is a graphical representation of an example of the properties of a control pattern used in a global shutter system.
Figure 8:
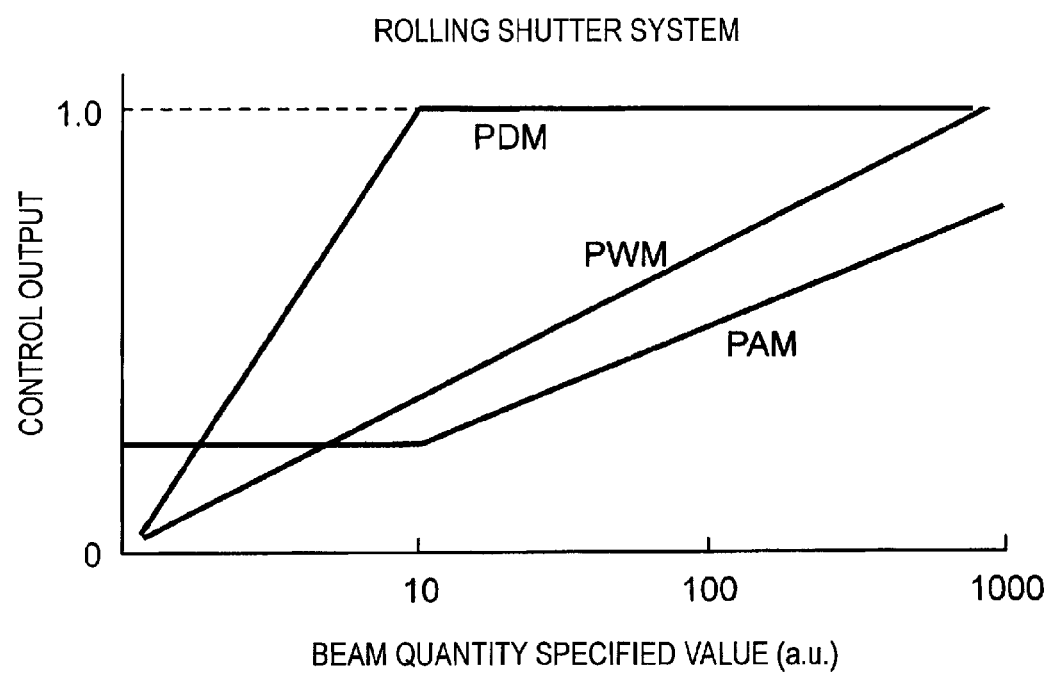
FIG. 8 is a graphical representation of an example of the properties of a control pattern used in a rolling shutter system.

FIGS. 7 and 8 respectively show the characteristics of two beam control tables which are different in the control pattern from each other. A control pattern shown in FIG. 7 is used to perform the control of a global shutter system, and a control pattern shown in FIG. 8 is used to perform the control of a rolling shutter system.

Referring to FIG. 7, this control pattern is constituted of a combination of three kinds of control characteristics, that is, the control characteristics of PNM control, control characteristics of PWM control, and control characteristics of PAM control. In the control pattern shown in FIG. 7, in the range of the beam quantity specified values of 0~10, there is output a PAM control value having a constant minimum amplitude and, at the same time, there is output a PNM control value which increases the beam quantity as the beam quantity specified value increases. When the beam quantity value exceeds 10, the PAM control value increases with an increase in the specified value and the PNM control value provides a constant value. The PWM control value varies in such a manner that, over the whole area of the beam quantity specified values of 0~1000, it increases the beam quantity with an increase in the beam quantity specified value. That is, in the case that there is employed the control pattern shown in FIG. 7, depending on the combinations of PNM control, PWM control and PAM control, the current to be applied to the beam source, that is, the beam quantity is determined.

Referring to FIG. 8, this control pattern is constituted of a combination of three kinds of control characteristics, that is, the control characteristics of PDM control, control characteristics of PWM control, and control characteristics of PAM control. According to the control pattern shown in FIG. 8, in the range of the beam quantity specified values of 0~10, there is output a PAM control value having a constant minimum amplitude and, at the same time, there is output a PDM control value which increases the beam quantity as the beam quantity specified value increases. When the beam quantity value exceeds 10, the PAM control value increases with an increase in the specified value and the PNM control value provides the maximum value (a constant value). The PWM control value varies in such a manner that, over the whole area of the beam quantity specified values of 0~1000, it increases the beam quantity with an increase in the beam quantity specified value. That is, in the case that there is employed the control pattern shown in FIG. 8, depending on the combinations of PDM control, PWM control and PAM control, the current to be applied to the beam source, that is, the beam quantity is determined.

The microcomputer 57, when it recognizes that the imaging device $11b$ of the endoscope 11 is a CCD image sensor of a global shutter system, selects automatically, for example, the beam control table of such control pattern as shown in FIG. 7. Therefore, in this case, the beam quantity of the beam source is controlled depending on the combinations of the PAM control, PNM control and PWM control. Here, although the PDM control can be further combined with the above pieces of control, in the case of the global shutter system, it is necessary to select the PDM control under the condition that it is limited to the shutter opening period (corresponding to the range of Tb shown in FIG. 6).

The microcomputer 57, when it recognizes that the imaging device $11b$ of the endoscope 11 is a CMOS image sensor of a rolling shutter system, selects automatically, for example, the beam control table of such control pattern as shown in FIG. 8. Therefore, in this case, the beam quantity of the beam source is controlled depending on the combinations of the PAM control, PDM control and PWM control.

In the case that the imaging device $11b$ of the endoscope 11 employs a global shutter system, the time during which the electronic shutter is opened is common in all pixels. Also, the radiation beam during closed period of the electric shutter is not used for photographing but leads to an increase in heat generation in the leading end portion of the endoscope 11 and in the portion to be observed. Therefore, in such situations, preferably, at least the PNM control may be performed to turn off the beam source for radiation while the electric shutter is closed, but it is not suitable to perform the PDM control which turns on the beam source continuously regardless of the opening/closing timing of the electronic shutter.

On the other hand, in the case that the imaging device $11b$ of the endoscope 11 is of a rolling shutter system, the time during which the electronic shutter is opened varies little by little in every line of pixel groups. Therefore, in this case, the beam source for radiation must be controlled to emit a beam continuously in such a manner that the radiation beam quantity is prevented from varying in every line. That is, the PNM control is not suitable but, preferably, the PDM control may be used to adjust the beam quantity.

In the above-mentioned endoscope system 100, the microcomputer 57 of the control unit 13 detects the type of the imaging device of the endoscope 11 connected and, according to the detected type, automatically switches the beam controlling system for radiation. Thus, even in the endoscope 11 which mounts thereon the imaging device 11*b* of any one of a global shutter system and a rolling shutter system, proper beam adjustment control can be performed.

Also, in the endoscope system 100, the beam source driver 43*b* of the control unit 13 controls the on beam quantity, on ratio, on time and on density of the beam source 43*a* in an integrated manner. Due to this, a proper radiation mode can be supplied according to the type and image pickup mode of the imaging device 11*b*. Also, due to the combination of the multiple pieces of control, the dynamic range of the beam control can be enlarged.

Figure 9:
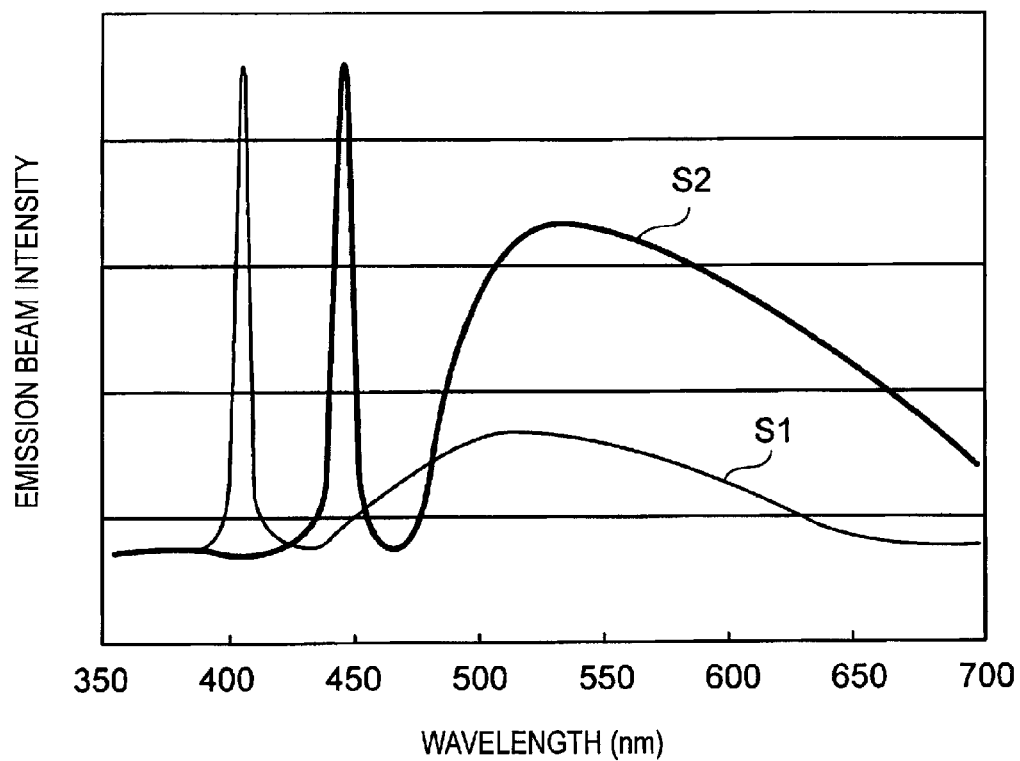
FIG. 9 is a graphical representation of a specific example of the spectrum of a radiation beam.

FIG. 9 shows a specific example of the spectra of the beam used for radiation in the endoscope system 100. A spectrum S1 shown in FIG. 9 represents a beam emission intensity distribution of such radiation beam by wavelengths as is radiated onto the portion to be observed of a living body or the like from the endoscope leading end portion 35 when a laser beam source having a center wavelength of 405 nm is employed as the beam source 43*a*. Also, a spectrum S2 represents a beam emission intensity distribution of such radiation beam by wavelengths as is radiated onto the portion to be observed of a living body or the like from the endoscope leading end portion 35 when a laser beam source having a center wavelength of 445 nm is employed as the beam source 43*a*.

For example, a laser beam of 445 nm, which is a blue beam, is emitted from the beam source 43*a*; and, this blue beam is guided to the radiation unit 11*a* of the endoscope 11 and is radiated onto the fluorescent member 72. In this case, part of the blue beam is absorbed by the fluorescent member 72 and the fluorescent member 72 is thereby excited to emit a beam. The beam emitted from the fluorescent member 72 is a visible beam having a wavelength band ranging from green to yellow. And, the remaining energy component of the blue beam, which is not absorbed by the fluorescent member 72 but is transmitted therethrough, and the beam emitted due to the excitation of the fluorescent member 72 are added together; and, the thus added beam is radiated onto the portion to be observed from the endoscope leading end portion 35 as a white radiation beam having such a wavelength distribution as the spectrum S2 shown in FIG. 9.

Similarly, when a laser beam of 405 nm is emitted by the beam source 43*a*, this laser beam is guided to the radiation unit 11*a* of the endoscope 11 and is then radiated onto the fluorescent member 72, this laser beam is radiated onto the portion to be observed from the endoscope leading end portion 35 as a radiation beam having such a wavelength distribution as the spectrum S1 shown in FIG. 9.

Next, description will be given below of several modifications of the radiation beam of the endoscope system 100.

Figure 10:
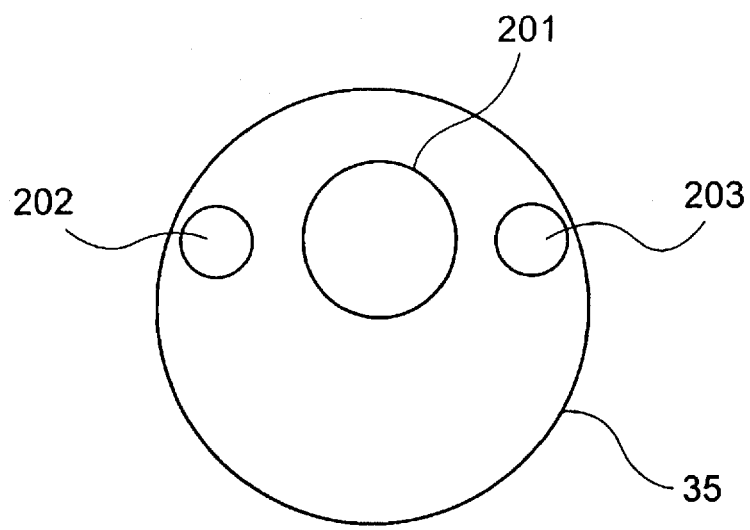
FIG. 10 is a front view of the structure of an endoscope leading end portion according to a first modification.

FIG. 10 is a structure view of the endoscope leading end portion 35 according to a first modification, showing a state in which the leading end side end face thereof is viewed from the portion to be observed. Also, FIG. 11 is a block diagram of the structure of a beam source apparatus 43 according to the first modification.

In the example shown in FIG. 10, in the endoscope leading end portion 35, there are formed one observation window 201 and two illumination windows 202 and 203 respectively disposed on both sides of the observation window 201. In the case that the two illumination windows 202 and 203 are disposed on both sides of the observation window 201 in this manner and radiation beams are respectively emitted from the two illumination windows 202 and 203, uneven radiation is hard to occur in an observation image; and, when a treating device is inserted through a forceps hole and is projected from the endoscope leading end, it is possible to prevent the treating device from showing its shadow in the observation image, and a sufficient beam quantity can be obtained over a wide range.

Figure 11:
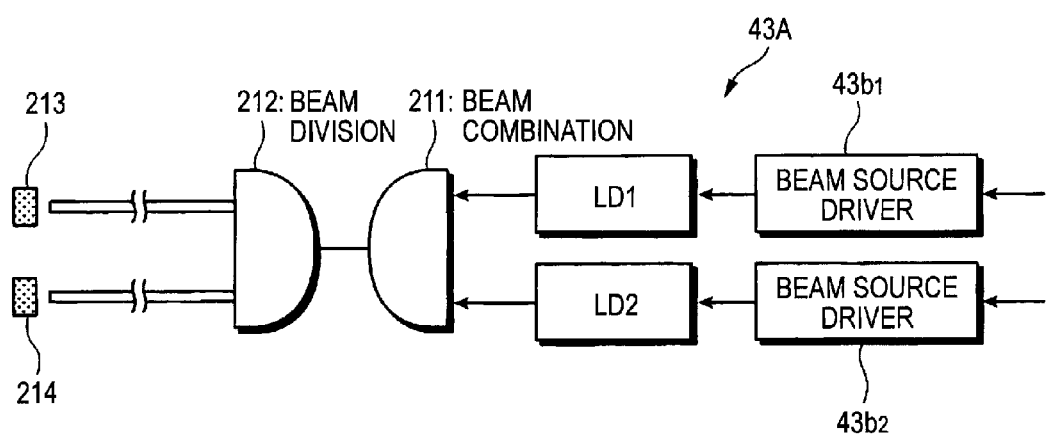
FIG. 11 is a block diagram of the structure of a beam source apparatus according to the first modification.

When the endoscope 11 shown in FIG. 10 is used, as the beam source 43, there is used, for example, a beam source apparatus 43A having such structure as shown in FIG. 11. The beam source apparatus 43A shown in FIG. 11 includes a laser beam source LD1 having a center wavelength of 445 nm and a laser beam source LD2 having a center wavelength of 405 nm.

The two laser beam sources LD1 and LD2 are respectively connected to two independent beam source drivers 43*b*1 and 43*b*2, while the emission beam quantities thereof are controlled individually. The emission beams of the two laser beam sources LD1 and LD2 are combined together by a combiner 211, while the combined beams are divided by a coupler 212 to multiple optical paths and are then radiated onto fluorescent members 213 and 214 respectively disposed in the beam emission ends of the respective optical paths.

Of the two laser beam sources LD1 and LD2, when only the laser beam source LD1 is turned on, there is emitted a white radiation beam for normal observation as a radiation beam. That is, the emission beams of the fluorescent members 213 and 214 generated due to the excitation of the fluorescent members 213 and 214 caused by the radiation of a laser beam having a center wavelength of 445 nm and the laser beam having a center wavelength of 445 nm transmitted through the fluorescent members 213 and 214 are added together, thereby providing a radiation beam having a spectrum near white.

Also, in the case that the two laser beam sources are turned on synchronously at such beam quantity ratio that LD1:LD2 is about 1:7, there can be obtained an observation image which is observed by a radiation beam for narrow bandwidth beam observation and in which fine blood vessels existing in the tissue surface layer are emphasized. Further, in the case that the two laser beam sources are turned on synchronously at such beam quantity ratio that LD1:LD2 is about 4:1, there can be obtained a hybrid radiation beam constituted of a white beam and a narrow bandwidth beam. According to this hybrid radiation beam, there can be obtained an observation image constituted of a normal observation image with information about the fine blood vessels of the tissue surface layer superimposed thereon.

Due to use of the two laser beam sources LD1 and LD2, there can be obtained a radiation beam having such spectra S1 and S2 as shown in FIG. 9. Also, in the case that a blue laser beam having a center wavelength of 445 nm and a violet laser beam having a center wavelength of 405 nm are emitted synchronously and are combined together, a wavelength band beam of about 460~470 nm, which is short in the blue laser beam having a center wavelength of 445 nm, can be compensated by a beam in the same band width which is emitted from the violet laser beam having a center wavelength of 405 nm, thereby being able to improve the color tone (color rendering properties) of the white beam.

Figure 12:
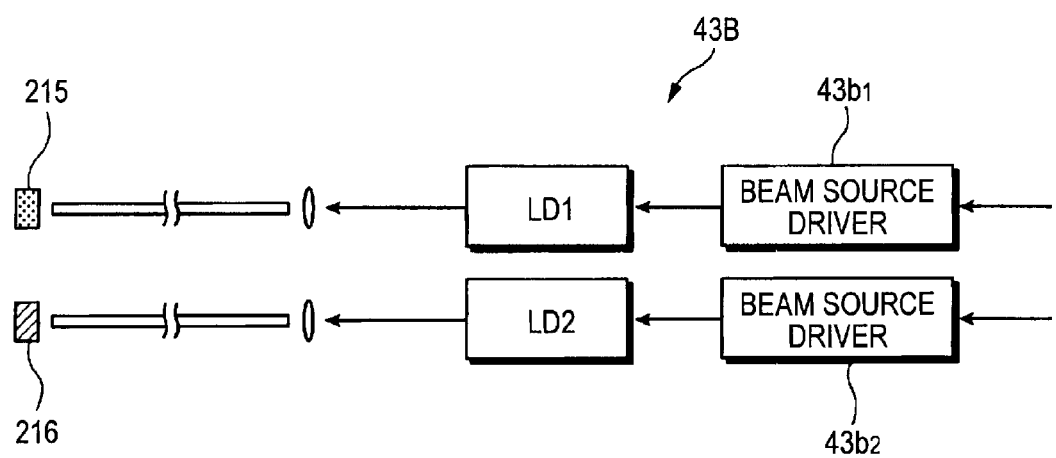
FIG. 12 is a block diagram of the structure of a beam source apparatus according to a second modification.

FIG. 12 shows the structure of the beam source apparatus 43 according to a second modification. In the case that the radiation beam can be emitted from the plural systems of illumination windows as shown in FIG. 10, for example, using the beam source apparatus 43B shown in FIG. 12, there may also be emitted from the plural systems of illumination windows beams which are different in spectrum from each other.

The beam source apparatus 43B shown in FIG. 12, similarly to the beam source apparatus 43A, includes a laser beam source LD1 having a center wavelength of 445 nm and a laser beam source having a center wavelength of 405 nm. The beams emitted from the laser beam sources LD1 and LD2 are not combined or divided. The emission beam of the laser beam source LD1 is at it is radiated onto a fluorescent member 215, while the emission beam of the laser beam source LD2 is guided through a diffusion member 216 to the illumination window. In this case, since the laser beam having a center wavelength of 405 nm can be radiated not through the fluorescent member, it can be used as a radiation beam while it remains as a narrow bandwidth beam. Thus, when carrying out a fluorescence observation or the like using an endoscope, there can be obtained an image which includes few noises.

Figure 13:
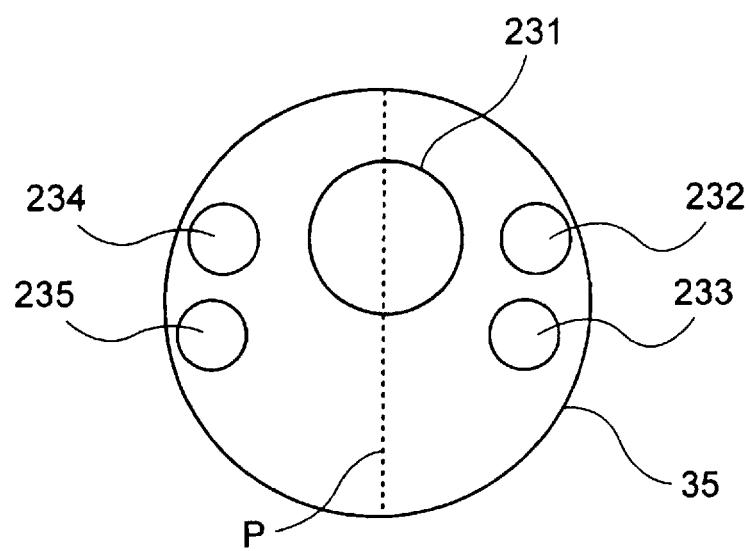
FIG. 13 is a front view of the structure of an endoscope leading end portion according to a third modification.

FIG. 13 is a structure view of an endoscope leading end portion 35 according to a third modification, showing a state in which the leading end side end face of the endoscope leading end portion 35 is viewed from the portion to be observed. Also, FIG. 14 is a block diagram of the structure of a beam source apparatus 43 according to the third modification.

According to the example shown in FIG. 13, in the endoscope leading end portion 35, there are formed one observation window 231 and two pairs of illumination windows (232, 233, 234 and 235) respectively disposed on both sides of the observation window 231. In the example shown in FIG. 13, the illumination windows 232 and 235 come as a pair, while the illumination windows 233 and 234 come as a pair. And, there is employed a structure in which, from the paired two illumination windows, there are emitted the same kinds of radiation beams. Due to use of the two pairs of illumination windows, there can be emitted synchronously beams which are different in spectrum from each other. That is, from one pair of illumination windows, there are emitted radiation beams respectively having a first spectrum; and, from the other pair of illumination windows, there are emitted radiation beams respectively having a second spectrum.

Here, the two pairs of illumination windows to be formed on both sides of the observation window are structured in the following manner. That is, while a straight line passing through the center point of the observation window and bisecting the leading end face of the insertion portion leading end is used as a boundary line P, the paired illumination windows are respectively disposed such that they stride over the boundary line P, one pair of first illumination windows (232 and 235) can serve as illumination windows for radiating a white beam, and the other pair of second illumination windows (233 and 234) can serve as illumination windows for radiating a narrow bandwidth beam which is narrower than the white beam.

Figure 14:
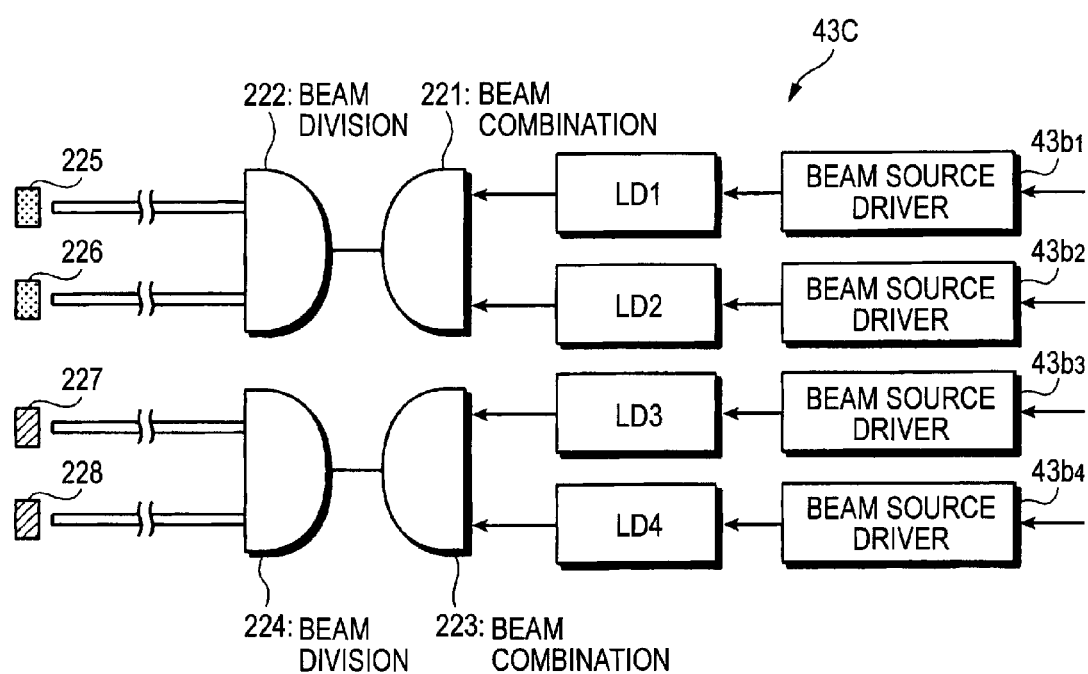
FIG. 14 is a block diagram of the structure of a beam source apparatus according to the third modification.

In the case that there is used the endoscope 11 shown in FIG. 13, as the beam source apparatus 43, there is used, for example, a beam source apparatus 43C having such a structure as shown in FIG. 14. The beam source apparatus 43C shown in FIG. 14 includes a laser beam source LD1 having a center wavelength of 445 nm, a laser beam source LD2 having a center wavelength of 405 nm, a laser beam source LD3 having a center wavelength of 472 nm and a laser beam source LD4 having a center wavelength of 780 nm.

The four laser beam sources LD1, LD2, LD3 and LD4 are respectively connected to their associated independent beam source drivers 43b1, 43b2, 43b3 and 43b4, while the emission beam quantities thereof can be controlled individually. The emission beams of the two laser beam sources LD1 and LD2 are combined together by a combiner 221, are divided to two optical paths by a coupler 222, and are radiated onto fluorescent members 225 and 226 respectively disposed on the beam emission ends of the respective optical paths. Also, the emission beams of the remaining two laser beam sources LD3 and LD4 are combined together by a combiner 223, are divided by a coupler 224 to two optical paths, and are guided to the illumination windows through diffusion members 227 and 228 respectively disposed on the beam emission ends of the respective optical paths.

According to the third modification having the structure shown in FIGS. 13 and 14, when LDs respectively having center wavelengths of 405 nm, 445 nm and 472 nm are turned on sequentially and the images of the portion to be observed are picked up, there can be extracted information about oxygen saturation from the observed image. Specifically, using a difference between the absorbance spectra of oxygenated hemoglobin $HbO_2$ and reduced hemoglobin Hb after release of oxygen respectively included in hemoglobin contained in an erythrocyte existing in blood, there can be obtained the oxygen saturation and blood depth of the observation area. Oxygenated hemoglobin $HbO_2$ and reduced hemoglobin Hb are substantially equal in the absorbance in the vicinity of a wavelength of 405 nm; in the vicinity of a wavelength of 445 nm, reduced hemoglobin Hb is higher in the absorbance than oxygenated hemoglobin $HbO_2$; and, in the vicinity of a wavelength of 472 nm, oxygenated hemoglobin $HbO_2$ is higher in the absorbance than reduced hemoglobin Hb. Also, a laser beam has such properties that the shorter the wavelength of the laser beam is, the shallower the reaching depth of the laser beam from the mucous tissue surface layer is. Using these properties, there can be obtained the oxygen saturation of the observation area and the blood depth that is projected on the observation area.

The laser beam having a center wavelength of 785 can be used properly to observe the blood information of the mucous tissue deep layer, thereby being able to perform an infrared beam observation using ICG (indocyanine green) and blood vessel navigation. This ICG, when in blood, provides a state in which it is connected to protein, absorbs a near infrared beam having a wavelength of, for example, 750~850 nm while the maximum absorbing wavelength is 805 nm, and emits near infrared fluorescence.

According to this radiation pattern, since there can be radiated a near infrared beam in addition to a white beam, there can be extracted, especially, the blood vessel information of the mucous tissue deep layer which is hard to obtain by a visible beam. For example, in the case that this beam projection unit is applied to an endoscope navigation system for obtaining information about the position of blood vessels existing around a bronchial tube, a laser beam having a center wavelength of 785 nm is radiated toward ICG charged into the blood vessels. In this case, in a portion where blood and ICG react with each other, there is emitted fluorescence having broad spectral characteristics and having a peak wavelength of 830 nm. By using the thus emitted fluorescence as a mark, the position accuracy can be enhanced and thus accurate treatment can be performed. Further, since there are used multiple beam projection units, by combining together beams from the respective beam projection units, beam radiation of high intensity can be realized.

Further, as the laser beam sources LD3 and LD4, there may also be used laser beam sources which can emit laser beams respectively having center wavelengths of 375 nm, 405 nm, 445 nm and the like. The laser beam having a wavelength of 375 nm provides an excitation beam when a fluorescent observation is performed using "luciferase" which is one of fluorescent medicines. Also, since the laser beams having the wavelengths of 405 nm and 445 nm can be radiated without passing through the fluorescent member, they can be radiated while they remain as the narrow bandwidth beams.

Although description has been given heretofore of the embodiment according to the invention, the invention is not limited to the embodiment. But, the invention also suggests that a person skilled in the art can make a change in the invention and apply the change to other similar system. Of course, such change falls under the scope of the invention.

As described below, the following contents are disclosed in this description.

(1) An endoscope system includes an endoscope, a control unit, a beam source control unit and a type check unit. The endoscope includes a radiation optical system for radiating a beam emitted from a beam source onto a subject and an imaging optical system containing an imaging device for imaging the subject. The endoscope removably connects to the control unit. The beam source control unit controls emission beam intensity of the beam source according to a beam quantity specified value input from the control unit. The type check unit checks a type of the imaging device mounted on the endoscope which is connected to the control unit. The beam source control unit has a plurality of control patterns for expressing a relationship between the beam quantity specified value and a control output value to be given to the beam source, switches to any one of the control patterns according to the check result obtained by the type check unit, and controls the emission beam intensity of the beam source according to the switched control pattern.

According to this endoscope system, even when the endoscope to be connected to the control unit mounts thereon any one of various types of imaging devices, the beam source control unit can switch to a control pattern corresponding to a currently specified imaging device, thereby being able to perform the optimum beam source control corresponding to the imaging device. Due to this, beam quantity control of a broad dynamic range is possible.

(2) The endoscope system according to (1), the beam source control unit switches the control pattern in linking with a shutter operation of the imaging device.

According to this endoscope system, since the control pattern is switched in linking with the shutter operation of the imaging device, there can be performed the optimum beam emission control for the shutter operation.

(3) The endoscope system according to (1) or (2), the type check unit checks the type of the imaging device as to whether the type is a global shutter system or a rolling shutter system.

According to this endoscope system, since the control pattern is changed according to the shutter system of an imaging device used, the optimum control can be performed on the respective imaging device. For example, in a global shutter system, preferably, the exposure times of the respective pixels may be set at the same timing in all pixels and, in the shutter closed time, there may be performed the control that turns off the beam source in order to avoid heat generation. Also, in a rolling shutter system, since the exposure times of the respective pixels vary in every scan line, it is necessary for the beam source to emit its beam continuously. Therefore, preferably, there may be performed the control that allows the actual exposure times of the respective lines to be uniform. Thus, the optimum control can be performed according to the type of the imaging device.

(4) The endoscope system according to (3), the control pattern specifies the emission beam intensity of the beam source corresponding to the beam quantity specified value based on at least three of control amounts. The control amounts include: a control amount corresponding to pulse number modulation control for changing lighting time of the beam source; a control amount corresponding to pulse width modulation control for changing duty ratio of lighting and lighting-out; a control amount corresponding to pulse amplitude modulation control for changing intensity of the lighting; and a control amount corresponding to pulse density modulation control for changing cycle of the lighting.

According to this endoscope system, correspondingly to a specified beam quantity value, the control amounts corresponding to be respectively performed by at least three of the pulse number modulation control, pulse width modulation control, pulse amplitude modulation control and pulse density modulation control are respectively obtained from the previously determined set value curves of the respective pieces of control, and the control amounts corresponding to be performed by the respective pieces of control are combined together to thereby specify the emission beam intensity of the beam source. Thus, due to combination of the respective control systems, in a broad dynamic range from a low output to a high output, the emission beam intensity can be set while maintaining its high continuous properties.

(5) The endoscope system according to (4), when the type check unit determines that the type of the imaging device is the global shutter system, the beam source control unit controls the beam source according to a control pattern constituted of a combination of the pulse number modulation control, pulse width modulation control and pulse amplitude modulation control.

According to this endoscope system, in the case of an imaging device of a global shutter system, by controlling the beam source according to a control pattern in which the pulse number modulation control, pulse width modulation control and pulse amplitude modulation control are combined together. Especially in the shutter closed time, the beam source can be turned off by the pulse number modulation control adjusting the turn-on time, thereby being able to prevent wasteful heat generation during the shutter closed time.

(6) The endoscope system according to (4), when the type check unit determines that the type of the imaging device is the rolling shutter system, the beam source control unit controls the beam source according to a control pattern constituted of a combination of the pulse density modulation control, pulse width modulation control and pulse amplitude modulation control.

According to this endoscope system, in the case of an imaging device of a rolling shutter system, by controlling the beam source according to a control pattern in which the pulse density modulation control, pulse width modulation control and pulse amplitude modulation control are combined together. Especially by the pulse density modulation control changing the lighting cycle, the beam source can be controlled in such a manner that the actual exposure times of the respective lines are set uniform.

(7) The endoscope system according to any one of (1) to (6), the endoscope includes a type check information storage unit which stores type information about the imaging device to be mounted on the endoscope. The type check unit reads out the type information about the imaging device from the type information storage unit of the endoscope connected to the control unit to determine the type of the imaging device.

According to this endoscope system, by reading out the type information of the imaging device from the type check information storage unit, the type of the imaging device can be determined simply and positively.

(8) The endoscope system according to any one of (1) to (7), the radiation optical system includes an optical fiber and a fluorescent member. The optical fiber guides the beam emitted from the beam source. The fluorescent member is disposed forwardly in an optical path of a beam emission end of the optical fiber to be excited by the emission beam so as to emit a beam. The radiation optical system mixes together the emission beam from the beam source and the emission beam from the fluorescent member to generate a radiation beam.

According to this endoscope system, since the emission beam from the beam source is mixed with the emission beam from the fluorescent member to thereby generate a radiation beam, for example, a blue excitation beam and fluorescence emitted due to excitation by the blue excitation beam are mixed together to thereby generate a white beam. That is, a radiation beam of an arbitrary color can be generated easily.

(9) The endoscope system according to any one of (1) to (8), the radiation optical system radiates beams respectively emitted from a plurality of beam sources. The beam source control unit drives the plurality of beam sources individually.

According to this endoscope system, by controlling the beam sources individually, the plurality of beams can be emitted from the same radiation optical system, which makes it possible to structure the endoscope leading end portion in a more compact and advantageous manner.

(10) The endoscope system according to any one of (1) to (9), the beam source is constituted of a semiconductor-light-emitting-element.

According to this endoscope system, a radiation beam can be generated with high responsibility and high efficiency.

What is claimed is:

1. An endoscope system comprising:
    an endoscope that includes a radiation optical system for radiating a beam emitted from a beam source onto a subject and an imaging optical system containing an imaging device for imaging the subject;
    a control unit to which the endoscope removably connects;
    a beam source control unit that controls emission beam intensity of the beam source according to a beam quantity specified value input from the control unit; and
    a type check unit that checks a type of the imaging device mounted on the endoscope which is connected to the control unit,
    wherein the beam source control unit has a plurality of control patterns for expressing a relationship between the beam quantity specified value and a control output value to be given to the beam source, switches to any one of the control patterns according to the check result obtained by the type check unit, and controls the emission beam intensity of the beam source according to the switched control pattern, the beam source control unit switches the control pattern in linking with a shutter operation of the imaging device, and the type check unit checks the type of the imaging device as to whether the type is a global shutter system or a rolling shutter system.

2. The endoscope system according to claim 1, wherein the control pattern specifies the emission beam intensity of the beam source corresponding to the beam quantity specified value based on at least three of control amounts, and the control amounts include: a control amount corresponding to pulse number modulation control for changing lighting time of the beam source; a control amount corresponding to pulse width modulation control for changing duty ratio of lighting and lighting-out; a control amount corresponding to pulse amplitude modulation control for changing intensity of the lighting; and a control amount corresponding to pulse density modulation control for changing cycle of the lighting.

3. The endoscope system according to claim 2,
    wherein, when the type check unit determines that the type of the imaging device is the global shutter system, the beam source control unit controls the beam source according to a control pattern constituted of a combination of the pulse number modulation control, pulse width modulation control and pulse amplitude modulation control.

4. The endoscope system according to claim 2,
    wherein, when the type check unit determines that the type of the imaging device is the rolling shutter system, the beam source control unit controls the beam source according to a control pattern constituted of a combination of the pulse density modulation control, pulse width modulation control and pulse amplitude modulation control.

5. The endoscope system according to claim 1,
    wherein the endoscope includes a type check information storage unit that stores type information about the imaging device to be mounted on the endoscope, and
    the type check unit reads out the type information about the imaging device from the type information storage unit of the endoscope connected to the control unit to determine the type of the imaging device.

6. The endoscope system according to claim 1,
    wherein the radiation optical system includes:
        an optical fiber which guides the beam emitted from the beam source: and
        a fluorescent member which is disposed forwardly in an optical path of a beam emission end of the optical fiber to be excited by the emission beam so as to emit a beam; and
    the radiation optical system mixes together the emission beam from the beam source and the emission beam from the fluorescent member to generate a radiation beam.

7. The endoscope system according to claim 1,
    wherein the radiation optical system radiates beams respectively emitted from a plurality of beam sources, and
    the beam source control unit drives the plurality of beam sources individually.

8. The endoscope system according to claim 1,
    wherein the beam source is constituted of a semiconductor-light-emitting-element.

* * * * *